US012791557B2

(12) United States Patent
Yoshizawa et al.

(10) Patent No.: US 12,791,557 B2
(45) Date of Patent: Nov. 10, 2026

(54) TEST REAGENT WITH AMELIORATED SIGNAL REDUCTION

(71) Applicant: Denka Company Limited, Tokyo (JP)

(72) Inventors: Eriko Yoshizawa, Niigata (JP); Yuki Shinohara, Niigata (JP); Shino Muramatsu, Niigata (JP); Miwa Kuwahara, Niigata (JP)

(73) Assignee: Denka Company Limited, Tokyo (JP)

(*) Notice: Subject to any disclaimer, the term of this patent is extended or adjusted under 35 U.S.C. 154(b) by 840 days.

(21) Appl. No.: 18/018,209

(22) PCT Filed: Jul. 21, 2021

(86) PCT No.: PCT/JP2021/027337
§ 371 (c)(1),
(2) Date: Jan. 26, 2023

(87) PCT Pub. No.: WO2022/024925
PCT Pub. Date: Feb. 3, 2022

(65) Prior Publication Data

US 2023/0273190 A1 Aug. 31, 2023

(30) Foreign Application Priority Data

Jul. 27, 2020 (JP) ................................ 2020-126241

(51) Int. Cl.
*G01N 33/543* (2006.01)
*G01N 33/531* (2006.01)
*G01N 33/569* (2006.01)

(52) U.S. Cl.
CPC ..... *G01N 33/54388* (2021.08); *G01N 33/531* (2013.01); *G01N 33/54387* (2021.08);
(Continued)

(58) Field of Classification Search
CPC .......... G01N 33/531; G01N 33/54387; G01N 33/54386; G01N 33/569; G01N 33/558;
(Continued)

(56) References Cited

U.S. PATENT DOCUMENTS

2004/0265800 A1 12/2004 Imoarai et al.
2006/0216695 A1 9/2006 Kamata et al.
(Continued)

FOREIGN PATENT DOCUMENTS

CN 107576785 A 1/2018
EP 2 523 001 A1 11/2012
(Continued)

OTHER PUBLICATIONS

PCT/JP2021/027337 Written Opinion mailed Jan. 31, 2023.*
(Continued)

*Primary Examiner* — Gailene Gabel
(74) *Attorney, Agent, or Firm* — Foley & Lardner LLP

(57) ABSTRACT

An object is to strongly suppress a false negative reaction and a false positive reaction, which cannot be sufficiently suppressed by a conventional method, in detection of an antigen such as a virus, a bacterium, or a protein to be detected in a specimen originated from a body fluid such as a nasal swab specimen, a nasal aspirate specimen, a nasal wash specimen, a blown snot specimen, a pharyngeal swab specimen, or a saliva specimen with a detection reagent utilizing an antigen-antibody reaction or a reaction between substances interacting with each other. The present invention provides a test reagent for detecting a target substance in a specimen by utilizing an antigen-antibody reaction or a binding reaction between substances interacting with each other, comprising a specimen extracting solution containing a chelating agent.

5 Claims, 1 Drawing Sheet

(52) U.S. Cl.
CPC ..... *G01N 33/54393* (2013.01); *G01N 33/569* (2013.01); *G01N 33/56983* (2013.01); *G01N 2469/00* (2013.01)

(58) Field of Classification Search
CPC ....... G01N 33/54388; G01N 33/54393; G01N 33/56983; G01N 33/588; G01N 2333/08; G01N 2469/00
See application file for complete search history.

(56) References Cited

U.S. PATENT DOCUMENTS

| | | | |
|---|---|---|---|
| 2015/0338395 | A1 | 11/2015 | Yamanaka et al. |
| 2016/0209410 | A1 | 7/2016 | Fukushima et al. |
| 2021/0080455 | A1 | 3/2021 | Horii et al. |

FOREIGN PATENT DOCUMENTS

| | | | | | |
|---|---|---|---|---|---|
| JP | 2003-279577 | A | | 10/2003 | |
| JP | 2004-301684 | A | | 10/2004 | |
| JP | 2005-024323 | A | | 1/2005 | |
| JP | 2011-099789 | A | | 5/2011 | |
| JP | 2016 099131 | | * | 5/2016 | ....... G01N 33/54386 |
| JP | 2016-099131 | A | | 5/2016 | |
| JP | 2017-166831 | A | | 9/2017 | |
| TW | 201508276 | A | | 3/2015 | |
| TW | I595009 | B | | 8/2017 | |
| TW | 201920958 | A | | 6/2019 | |

OTHER PUBLICATIONS

Office Action dated Apr. 8, 2025 in JP 2020-126241.
International Search Report dated Sep. 28, 2021 in PCT/JP2021/027337.
Supplementary European Search Report dated Nov. 20, 2023 in EP 21851287.9.

* cited by examiner

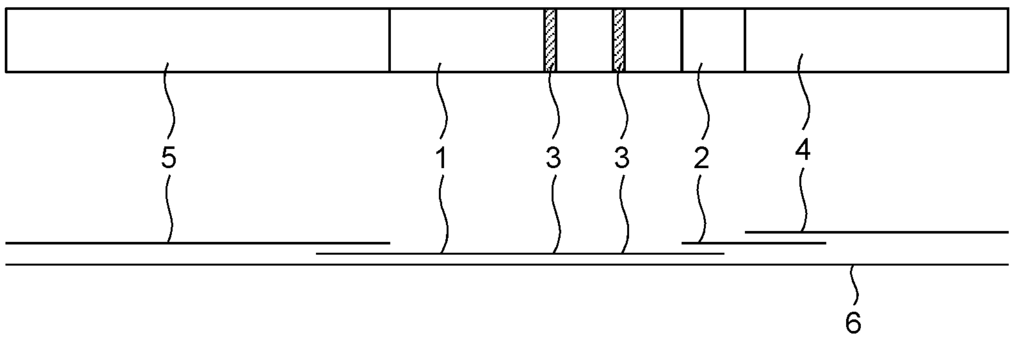
5
1
3
3
2
4
6

TEST REAGENT WITH AMELIORATED SIGNAL REDUCTION

CROSS-REFERENCE TO RELATED APPLICATIONS

This application is the U.S. National Stage of PCT/JP2021/027337, filed Jul. 21, 2021, which claims priority to JP 2020-126241, filed Jul. 27, 2020.

TECHNICAL FIELD

The present invention relates to a technique capable of strongly suppressing, by using a a specimen extraction solution containing a chelating agent, a false negative reaction and a false positive reaction, which cannot be sufficiently suppressed by a conventional method when detecting substances such as a virus/microbe, or a protein to be detected in a specimen originated from a body fluid such as a nasal swab specimen, a nasal aspirate specimen, a nasal wash specimen, a blown snot specimen, a pharyngeal swab specimen, or a saliva specimen, with a detection reagent utilizing an antigen-antibody reaction or a binding reaction between substances interacting with each other.

BACKGROUND ART

In recent years, various diagnostics reagents and kits detecting whether someone has infectious diseases caused by a pathogen such as a virus or microbe, or to check pregnancy have been continuously developed, utilizing an antigen-antibody reaction or a binding reaction between substances interacting with each other. In any of such test reagents, a pretreatment process for creating conditions suitable for a detection reaction is included after collecting a specimen from a patient, and this process is important for obtaining an accurate result. In particular, many of those test reagents with simple procedures have characteristics that no special facility is needed, and that they are easy to operate, and are inexpensive, and hence, are widely used not only in large hospitals and medical testing centers but also in general hospitals and clinics, and are often handled by users that are not specialists for the test. Therefore, it is very important that a reagent is highly accurate. Examples of those tests that are currently commercially available include a test reagent for detecting agents that cause infectious diseases, and a test reagent to check pregnancy. Such a test reagent is used, in many cases, in a medical institution where a patient first visits, a specimen collected from the patient can be used on the spot to determine infection or pregnancy, and hence a treatment and the like can be conducted at an early stage, and thus, significance of a rapid test reagent in medical care has been increasing. In accordance with increase of the use of rapid test reagents, users demand, as performances of reagents, for test results with higher reproducibility and higher test accuracy.

Currently, as a representative reagent for a rapid test method, an immunoassay using an antigen-antibody reaction, particularly, immunochromatography is generally known. In the immunochromatography, a complex consisting of a capturing material (capturing substance) specifically binding to a substance to be detected, and a labeling material specifically binding to the substance to be detected is formed on a membrane, and by detecting/quantitatively measuring the labeled substances, target substance can be detected. The immunochromatography is designed in a simple measurement device, and is also excellent in cost, and hence is widely employed for detecting a variety of substances to be detected.

In one aspect of the immunochromatography, in a test device including a detection part in which an antibody specifically binding to a target substance is immobilized as a capturing substance on a membrane strip of nitrocellulose or the like, and a labeled material part including a labeled substance specifically binding to the substance to be detected, a specimen sample containing the target substance is added to be developed making a complex of the target substance—the labeling material, and the complex is then captured on the detection part to detect or quantitatively determine the labeling.

In recent years, clinical diagnostic agents including immunochromatography are desired to provide more highly reliable diagnostic results in clinical practice, and there has arisen a problem of further improvement of reliability of a reagent. A test reagent having high reliability refers to a test reagent having high sensitivity and specificity, and minimally making erroneous interpretation. Particularly regarding specificity, there always exists a technical problem how reagent design can cope with variety of specimen components derived from a difference in backgrounds among respective patients, and in the simple and rapid test method, it is becoming more important to avoid a nonspecific reaction more effectively. To solve these problems, it has been reported that specificity is improved to some extent by contacting a basic amino acid such as arginine or lysine, an inorganic salt, glycine ethyl ester, a surfactant, or an animal-derived immunoglobulin with a specimen (see Patent Literatures 1, 2 and 3), but all of these have merely limited effects, and there still exists a nonspecific reaction that cannot be suppressed. Therefore, there is a demand for a technique for further strongly improving specificity without reducing sensitivity.

CITATION LIST

Patent Literature

Patent Literature 1: JP Patent Publication (Kokai) No. 2003-279577 A
Patent Literature 2: JP Patent Publication (Kokai) No. 2005-24323 A
Patent Literature 3: JP Patent Publication (Kokai) No. 2004-301684 A

SUMMARY OF INVENTION

Technical Problem

When detecting substances such as a virus/microbe, or a protein to be detected in a specimen originated from a body fluid such as a nasal swab specimen, a nasal aspirate specimen, a nasal wash specimen, a blown snot specimen, a pharyngeal swab specimen, or a saliva specimen, with a detection reagent utilizing an antigen-antibody reaction or a binding reaction between substances interacting with each other, a false positive reaction or a false negative reaction that cannot be sufficiently suppressed by a conventional method still exists, and thus prevents accurate diagnosis. In the present invention, a test reagent employing a specimen extracting solution or a specimen extraction method including a component capable of strongly suppressing a false negative reaction and a false positive reaction without reducing sensitivity is provided.

Solution to Problem

The present inventors earnestly searched for a method for more strongly suppressing a nonspecific reaction occurring in using, as a testing sample, a specimen derived from a body fluid, such as a nasal swab specimen, a nasal aspirate specimen, a nasal wash specimen, a blown snot specimen, a pharyngeal swab specimen or a saliva specimen, and as a result, have found a component capable of suppressing signal reduction more remarkably than in a conventional method, and further found that a false negative reaction detected in a conventional method can be suppressed by adding this component to a specimen extracting solution or a materials or the like to be contacted with the specimen in a process performed before or simultaneously with a detection reaction, and thus, the present invention was accomplished.

Specifically, the present invention provides the following:

[1] A test reagent that is a test kit for detecting a target substance in a specimen by utilizing an antigen-antibody reaction or a binding reaction between substances interacting with each other, comprising a specimen extracting solution containing a chelating agent.

[2] The test reagent according to [1], for suppressing signal reduction.

[3] The test reagent according to [1] or [2], wherein the specimen extracting solution further comprises a surfactant.

[4] The test reagent according to any one of [1] to [3], wherein the test reagent is an immunochromatographic test kit comprising an immunochromatographic test device and the specimen extracting solution containing the chelating agent.

[5] The test reagent according to any one of [1] to [3], wherein the test reagent is an immunochromatographic test device, comprising a portion impregnated with the specimen extracting solution containing the chelating agent.

[6] The test reagent according to any one of [1] to [5], wherein the specimen extracting solution comprises the chelating agent with a concentration of 8 mM to 300 mM.

[7] The test reagent according to [6], wherein the specimen extracting solution comprises the chelating agent with a concentration of 25 mM to 300 mM.

[8] The test reagent according to any one of [1] to [7], wherein the chelating agent is selected from the group consisting of ethylenediaminetetraacetic acid (EDTA), glycoletherdiaminetetraacetic acid (EGTA), 1,3-propanediaminetetraacetic acid (PDTA), and nitrilotriacetic acid (NTA).

[9] A method for detecting, by utilizing an antigen-antibody reaction or a reaction between substances interacting with each other, a target substance selected from the group consisting of a viral antigen, a bacterial antigen, and a protein antigen in a specimen selected from the group consisting of a nasal swab specimen, a nasal aspirate specimen, a nasal wash specimen, a blown snot specimen, a pharyngeal swab specimen, and a saliva specimen, wherein detection is performed with signal reduction suppressed by previously contacting the specimen with a chelating agent.

[10] The method according to [9], wherein the method for detecting the target substance is immunochromatography, the method comprising putting the specimen in a specimen extracting solution containing the chelating agent, and adding the specimen extracting solution to an immunochromatographic test device.

[11] The method according to [9], wherein the method for detecting the target substance is immunochromatography, the method comprising adding the specimen to an immunochromatographic test device including a portion impregnated with a specimen extracting solution composition containing the chelating agent.

[12] The method according to [10] or [11], wherein the specimen extracting solution further contain a surfactant.

[13] The method according to any one of [9] to [12], wherein the specimen extracting solution containing the chelating agent with a concentration of 8 mM to 300 mM is used.

[14] The method according to [13], wherein the specimen extracting solution containing the chelating agent with a concentration of 25 mM to 300 mM is used.

[15] The method according to any one of [9] to [14], wherein the chelating agent is selected from the group consisting of ethylenediaminetetraacetic acid (EDTA), glycoletherdiaminetetraacetic acid (EGTA), 1,3-propanediaminetetraacetic acid (PDTA), and nitrilotriacetic acid (NTA).

The present description encompasses the disclosed contents of Japanese Patent Application No. 2020-126241, based on which the present application claims the benefit of priority.

Advantageous Effects of Invention

According to the present invention, regarding a detection reagent for detecting a specific virus, bacterium, protein, low molecular compound or the like by utilizing an antigen-antibody reaction or a binding reaction between substances interacting with each other in a specimen or the like derived from a body fluid such as a nasal swab specimen, a nasal aspirate specimen, a nasal wash specimen, a blown snot specimen, a pharyngeal swab specimen or a saliva specimen, a test reagent that more strongly suppresses signal reduction caused by mixture of the specimen, and has high reproducibility, and high test accuracy can be provided. Besides, erroneous clinical diagnosis caused by a nonspecific reaction can be more definitely prevented, which is useful for both patients and users such as doctors, laboratory technicians, and nurses.

BRIEF DESCRIPTION OF DRAWING

FIG. 1 is a diagram illustrating the structure of a test device used in the present invention.

DESCRIPTION OF EMBODIMENT

Now, the present invention will be described in detail.

The present invention is a method for suppressing a false negative reaction and a false positive reaction and preventing signal reduction, namely, sensitivity reduction, by contacting a chelating agent with a specimen in detecting a target substance in the specimen with a detection reagent utilizing an antigen-antibody reaction or a binding reaction between substances interacting with each other.

In the present invention, an antibody encompasses an antigen-binding fragment of an antibody.

(Specimen)

A specimen to be used is not limited. Examples of the specimen include a pharyngeal swab, a nasal swab, a nasal aspirate, a throat wash, a nasal wash, a blown snot, and saliva. These are designated as a pharyngeal swab specimen, a nasal swab specimen, a nasal aspirate specimen, a throat wash specimen, a nasal wash specimen, a blown snot specimen, and a saliva specimen. These specimens can be diluted with a buffer to be used, or can be directly used without dilution.

(Target Substance)

A target substance is also not limited at all, and may be any substance desired to be detected. Specific examples include viral antigens such as influenza virus, adenovirus, RS (respiratory syncytial) virus, human metapneumovirus (hMPV), hepatitis A virus (HAV), hepatitis B virus (HBV), human immunodeficiency virus (HIV), norovirus, and corona viruses such as SARS-CoV, MERS-CoV, and SARS-CoV2, and bacterial antigens such as methicillin-resistant *Staphylococcus aureus* (MRSA), Group A *Streptococcus*, Group B *Streptococcus*, and bacteria belonging to the genus *Legionella*; toxins produced by bacteria and the like; *mycoplasma* antigens; *Chlamydia* antigens such as *Chlamydia trachomatis*; protozoan antigens; fungal antigens; hormones such as human chorionic gonadotropin; proteins such as C-reactive protein, myoglobin, cardiac troponin, and procalcitonin; various tumor markers; and antigens such as agricultural chemicals and endocrine disruptors, and further include antibodies to the above-described bacteria, viruses and the like.

(Collection of Specimen)

A method for collecting a specimen is not also limited at all, and examples include a method in which a pharyngeal swab specimen, a nasal swab specimen, a nasal aspirate specimen, a throat wash specimen, a nasal wash specimen, a blown snot specimen, or a saliva specimen is collected with a specimen collection device such as a swab, and a method in which the specimen is collected through aspiration or the like with an aspirator.

(Contact between Chelating Agent and Collected Specimen)

In the method of the present invention, the specimen is contacted with a chelating agent. Here, the specimen is contacted with a chelating agent, and as a result, false negative and false positive can be suppressed in measurement of the specimen. In the contact of the specimen with the chelating agent, a target substance is contacted with the chelating agent, and therefore, in the method of the present invention, this contact is referred to also as contact of the target substance with the chelating agent. Besides, contact of the specimen with the chelating agent is referred to also as treatment of the specimen with the chelating agent in some cases.

Besides, a specimen extracting solution refers to a liquid in which a target substance contained in a specimen is suspended for easing measurement, but there is no need to extract a target substance from, for example, a cell or the like through dissolution or the like, and the specimen extracting solution can be simply referred to as a specimen treatment solution, a specimen dilute solution, or a specimen suspension solution.

In the present invention, the specimen and the chelating agent need to contact with each other before being used in a test. Here, the term "before being used in a test" refers to before reacting the target substance contained in the specimen with a corresponding antibody or antigen, or before reacting the target substance contained in the specimen with a substance interacting therewith. A reaction with an antibody or antigen refers to binding to the antibody or antigen, and a reaction with a substance interacting with the target substance contained in the specimen refers to binding to the interacting substance.

Examples of a method for contacting the chelating agent with the specimen of the present invention include a method in which the specimen is added to a solution containing the chelating agent, and the resultant is mixed for contact, and a method in which a specimen extracting solution containing the chelating agent is caused to be included in a test device to be used for measurement, and the specimen is added to the test device to be used for the test to contact the specimen with the chelating agent.

A specific example of the method in which the specimen is mixed with the solution containing the chelating agent for the contact includes a method in which the chelating agent is contained in a specimen extracting solution containing the collected specimen suspended or dispersed therein, and the specimen is contacted with the chelating agent by adding the specimen to the specimen extracting solution to be mixed. For example, in using a specimen extracting solution containing the chelating agent, if the specimen is a nasal swab, a nasal swab is collected with a swab, and the swab thus soaked with the collected specimen is put in the specimen extracting solution to suspend or disperse and extract the specimen therein, and thus, the specimen can be contacted with the chelating agent.

A specific example of the method in which the test device to be used for measurement is caused to include the specimen extracting solution containing the chelating agent, and the specimen is added to the test device to contact the specimen with the chelating agent includes a method in which a fibrous or porous materials, such as a filtration filter, included in a test device is caused to include a specimen extracting solution containing the chelating agent, and the specimen is contacted with the chelating agent included in the fibrous or porous materials in adding the collected specimen to the test device. An example of such a test device includes an immunochromatographic device described below.

A material of the porous substrate of the test device is not limited at all, and examples include pulp, cotton, wool, polyester, polypropylene, nylon, acrylic glass fiber, and nitrocellulose. When the test device to be used for measurement is prepared with the specimen extracting solution containing the chelating agent, and the specimen is contacted with the chelating agent by adding the specimen to the test device, for example, the specimen extracting solution containing the chelating agent is impregnated into the porous materials, and the resultant is dried, and in a process performed before or simultaneously with a reaction for detecting the target substance on the test device, the specimen may be contacted with the porous materials. For example, when the specimen is added to the test device, the specimen is developed on the test device, and then reaches a portion where the reaction occurs on the device to cause a reaction such as an antibody-antigen reaction. When the porous materials having been prepared to include the specimen extracting solution containing the chelating agent is provided in a position in prior to the position where the reaction occurs on the test device, the specimen contacts with the chelating agent before the reaction. For example, a filtration filter is used as the porous material, and the filtration filter including the specimen extracting solution containing the chelating agent may be provided in a position where the specimen is added. In this case, if a nasal swab is used as the specimen, a swab is used to collect the nasal swab, and the swab thus soaked with the collected specimen is put in a specimen extracting solution having an arbitrary composition not containing the chelating agent to disperse or dissolve the specimen therein, and then, the filtration filter having been prepared to include the chelating agent as described above, that is, a constituting materials of the test device, is impregnated with the specimen extracting solution, and thus, the specimen can be contacted with the chelating agent.

(Chelating Agent and Concentration Thereof)

Examples of the chelating agent used in the method of the present invention include ethylenediaminetetraacetic acid (EDTA), glycoletherdiaminetetraacetic acid (EGTA), 1,3-propanediaminetetraacetic acid (PDTA), and nitrilotriacetic acid (NTA). These chelating agents encompass sodium salts and potassium salts.

As described above, the chelating agent is contained in a specimen extracting solution, a filtration filter or the like as the specimen extracting solution. For suppressing a false negative reaction, the concentration of the chelating agent is preferably 8 mM or more, more preferably 10 mM or more, and further preferably 50 mM or more. Besides, a plurality of these chelating agents can be simultaneously used, and in this case, a total concentration of the chelating agents is also preferably 8 mM or more, more preferably 10 mM or more, and further preferably 50 mM or more. Furthermore, for suppressing a false positive reaction, the concentration of the chelating agent is preferably 25 mM or more, more preferably 40 mM or more, and further preferably 50 mM or more. An upper limit of the concentration of the chelating agent needs not be determined, but is, for example, 1000 mM or less, 500 mM or less, 300 mM or less, or 150 mM or less. For example, when the chelating agent is used in a concentration range of 25 mM to 300 mM, 40 mM to 300 mM, or 50 mM to 300 mM, both a false negative reaction and a false positive reaction can be satisfactorily suppressed. Besides, when it is used in a concentration of 150 mM or less, reduction of coloring intensity can be suppressed. Also, when the specimen extracting solution containing the chelating agent is caused to be included in a porous substrate such as a filtration filter, the chelating agent in the above-described concentration may be caused to be included in the porous materials.

(Other Components Used in Addition to Chelating Agent)

The specimen extracting solution of the present invention or the specimen extracting solution to be impregnated in a member such as a porous material or the like to be contacted with the specimen in a process before a detection reaction may contain, in addition to the chelating agent, a known substance capable of reducing a nonspecific reaction, a surfactant, a pH buffering component, various proteins, salts, and sugars. Examples of the component capable of reducing a nonspecific reaction include arginine, arginine ethyl ester, arginine methyl ester, glycine ethyl ester, glycine methyl ester, lysine, and various isomers of these compounds. Examples of the surfactant include nonionic surfactants such as polyethylene glycol mono-p-isooctylphenyl ether, and polyoxyethylene sorbitan monolaurate, amphoteric surfactants such as CHAPS and laurylamide sulfobetaine, anionic surfactants such as sodium dodecylsulfate, and cationic surfactants such as dodecyltrimethylammonium chloride. The concentration of the surfactant in the specimen extract is preferably 0.5 to 5 (w/v) %, more preferably 1 to 3 (w/v) %, and further preferably 1.5 to 2.5 (w/v) %. A surfactant has a virucidal effect, and the effect is increased when a chelating agent exists at the time of virus destruction with the surfactant. Accordingly, it is preferable that both the surfactant and the chelating agent are present in the specimen extracting solution.

Examples of the buffering component include a phosphate buffer, a Tris buffer, and Good's buffer. Examples of the protein component include BSA (bovine serum albumin), casein, gelatin, and IgG. Examples of the salts include lithium chloride, sodium chloride, potassium chloride, sodium bromide, potassium bromide, sodium iodide, and potassium iodide.

(Detection Method)

In the method of the present invention, detection is performed by a method utilizing an antigen-antibody reaction or a binding reaction between substances interacting with each other. Examples of a combination of the substances interacting with each other include a combination of a ligand and a receptor, a combination of receptors, and a combination of biotin and avidin or streptavidin.

The method is not especially limited as long as it is a detection method utilizing an antigen-antibody reaction or substances interacting with each other, and examples include immunochromatography, latex agglutination, turbidimetric immunoassay, immunonephelometry, chemiluminescent enzyme immunoassay (CLEIA), enzyme immunoassay (EIA) such as enzyme linked immunosorbent assay (ELISA), and include latex agglutination, turbidimetric immunoassay, and immunonephelometry. Many of these methods are immunological methods, and utilize an antigen-antibody reaction, but can also utilize, instead of the antigen-antibody reaction, a reaction between substances interacting with each other. Among these methods, sandwich methods are preferred. In a representative sandwich method, a first substance to be bound to a target substance is immobilized on a specific support as a capturing substance for the target substance. Besides, a second substance to be bound to the target substance and having been labeled is prepared to bind to the target substance. Then, a complex of "the first substance to be bound to the target substance—the substance to be detected—the second substance to be bound to the target substance and having been labeled" (wherein "—" indicates a bond) is formed, and the target substance is measured by a signal emitted from the labeled substance. The first substance to be bound to the target substance, and the second substance to be bound to the target substance may be the same. The target substance, and the substance to be bound to the target substance may be an antigen and an antibody, or an antibody and an antigen, or may be substances interacting with each other. As a solid phase on which the first substance to be bound to the target substance is immobilized, any of all materials on which a substance such as a protein can be immobilized by known techniques can be used, and for example, known materials such as a porous thin film (membrane) having capillary action, a particulate matter, a test tube, and a resin plate can be arbitrarily selected. Besides, as a substance for labeling the second substance to be bound to the substance to be detected, an enzyme, a radioisotope, a fluorescent material, a luminescent material, a colored particle, a colloidal particle, and the like can be used.

Among the sandwich methods, from the viewpoints of simplicity and promptness of a clinical test, immunochromatography, that is, lateral flow immunoassay using a membrane, is particularly preferred. Now, general immunochromatography utilizing an antigen-antibody reaction will be described. An immunochromatographic test device is illustrated in FIG. 1.

An upper portion of FIG. 1 is a top view, and a lower portion is a cross-sectional view. The test device includes various portions laminated on a nitrocellulose membrane (1) laminated on a plastic plate (6). In the illustrated specific example, the nitrocellulose membrane (1) having two detection parts (3) formed thereon from a capturing substance for a target substance such as an antibody, an absorption pad part (5) made from filter paper, a labeling material part (2), and a sample addition part (4) made from a glass fiber filter are respectively laminated on the plastic plate (6).

In addition, as illustrated in the drawing, one end region of the absorption pad part (5) and one end region of the nitrocellulose membrane (1) are overlapped each other, the other end region of the nitrocellulose membrane (1) and one end region of the labeling material part (2) are overlapped each other, and the other end region of the labeling material part (2) and one end region of the sample addition part (4) are overlapped each other, and thus, a continuous lateral flow path is formed.

The labeling material part (2) contains a labeling material in which a labeling substance is chemically or physically bound to the capturing substance for a substance to be detected such as an antibody. Examples of the labeling substance include a gold colloidal particle, a platinum colloidal particle, a color latex particle, a magnetic particle, an enzyme, a quantum dot, a fluorescent dye or a fluorescent material. The labeling material part is made of a porous substrate including the labeling material, and as a material of the substrate, generally used glass fiber, unwoven fabric and the like can be used. A porous substrate obtained by impregnating with the labeling material and drying is designated also as a stabilized dried labeling pad. In other words, the labeling material part is a section including the stabilized dried labeling pad that contains an antibody to be bound to the target substance through an antigen-antibody reaction and has been labeled with a colored latex particle.

Each detection part (3) is a section on which antibodies to be bound to the target substance through an antigen-antibody reaction are immobilized in a line shape as a capturing substance.

Examples of the materials or the like to be contacted with the specimen in the process performed before the detection reaction of the target substance, or simultaneously with the detection reaction include the parts (1), (2) and (4) described above, but is not limited to these parts as long as it is a material to be contacted with the specimen in the process performed before the detection reaction of the target substance or simultaneously with the detection reaction. When the specimen is added to the sample addition part (4), the specimen flows from the sample addition part (4) toward the absorption pad part (5). Assuming that the flow from the sample addition part (4) toward the absorption pad part (5) is expressed as an upstream to downstream flow, it can be said that the material to be contacted with the specimen in the process performed before the detection reaction of the target substance or simultaneously with the detection reaction is present upstream from a portion where the detection reaction occurs.

Next, the immunoassay using this test device will be described. First, a specimen is suspended in a specimen extraction solution to prepare a specimen sample where a substance to be detected is extracted. The specimen sample is dropped onto a sample addition part (4) of the test device. The specimen sample containing the target substance is mixed with the labeling material part (2), while moving horizontally on the membrane, and dissolves the labeling material. When the target substance is present in the specimen sample, a complex of the target substance—the labeling material is formed. When the complex reaches the detection part (3), a complex of the capturing antibody—the target substance—the labeling material is formed on the line. The presence of the complex is detected in accordance with a signal emitted from the labeling substance contained in the complex, and thus, the presence of the target substance in the specimen can be determined. Other components and the like not involved in the reaction are absorbed by the absorption pad part (5). In the example illustrated in FIG. 1, there are two detection parts (3), and these are for capturing two types of target substances, such as influenza A virus and influenza B virus. When such a plurality of detection parts (3) are provided, immunoassay of a plurality of types of substances to be detected can be simultaneously performed.

In the immunochromatography described above, the chelating agent may be contained in the specimen extracting solution to be mixed with the specimen for extracting the target substance, or the chelating agent may be contained in the nitrocellulose membrane (1), the labeling material part (2), and/or the sample addition part (4) of the immunochromatographic test device.

The present invention encompasses a test reagent utilizing an antigen-antibody reaction or a binding reaction between substances interacting with each other. The test reagent refers to a test device itself in some cases, and refers to a test kit including the test device and another reagent in other cases. The test reagent of the present invention encompasses a test kit including an immunochromatographic test device, and a specimen extracting solution containing a chelating agent. Alternatively, the test reagent of the present invention encompasses an immunochromatographic test device equipped with a portion including a specimen extracting solution containing a chelating agent.

EXAMPLES

The present invention will now be specifically described by way of the following examples, and it is noted that the present invention is not limited to these examples.

In the following examples, an example in which a non-specific reaction in a specimen is suppressed in an immunochromatographic kit for detecting hMPV (human metapneumovirus) in using a specimen extraction solution of the present invention will be described.

Preparation Example

1. Preparation of Anti-hMPV Monoclonal Antibody

A BALB/c mouse immunized with hMPV antigen was raised for a prescribed period of time, and the spleen was excised from the resultant mouse to be fused with mouse myeloma cells (P3×63) by a method of Kohler et al. (Kohler et al., Nature, vol. 256, p. 495-497 (1975)). The thus obtained fused cells (hybridomas) were retained in an incubator at 37° C., and cell purification (monocloning) was performed with antibody activity of a supernatant checked by ELISA using a plate having hMPV antigen immobilized thereon. The thus obtained two strains of cells were respectively administered into the abdominal cavities of pristane-treated BALB/c mice, and after about 2 weeks, an antibody-containing ascites fluid was collected from each mouse.

From each of the thus obtained ascites fluids, IgG was purified by affinity chromatography using a protein A column, and thus, two types of purified anti-hMPV antibodies were obtained.

2. Immobilization of Anti-hMPV Antibody onto Nitrocellulose Membrane

A solution obtained by diluting the purified anti-hMPV antibody with purified water to 1.0 mg/mL was applied in the shape of a line in a prescribed position on a nitrocellulose membrane lined with a PET film, and the resultant was dried at 45° C. for 30 minutes to obtain an anti-hMPV antibody immobilized membrane (hereinafter referred to as the antibody immobilized membrane).

3. Immobilization of Anti-hMPV Antibody onto Colored Polystyrene Particle

The other purified anti-hMPV antibody, not used for the immobilization on the nitrocellulose membrane, was diluted with purified water to 1.0 mg/mL, a colored polystyrene particle (manufactured by Thermo Scientific) was added thereto to 0.1 (w/v) %, the resultant was stirred, and then carbodiimide was added thereto to 1 (w/v) %, followed by further stirring. A supernatant was removed by centrifugation, and the resultant was resuspended in 50 mM Tris (pH 9.0) and 3 (w/v) % BSA to obtain an anti-hMPV antibody binding colored polystyrene particle.

4. Application/Drying of Anti-hMPV Antibody Binding Colored Polystyrene Particle The anti-hMPV antibody binding colored polystyrene particle obtained as described above in 3. was applied, in a prescribed amount of 1.0 μg, on a glass fiber unwoven fabric, and the resultant was dried at 45° C. for 30 minutes.

5. Adhering of Immobilized Membrane, Dried Pad, and Other Members

The antibody immobilized membrane and the dried pad prepared as described above in 2. and 4. were adhered to other members (a backing sheet, an adsorption band, and a sample pad), and the resultant was cut into a width of 5 mm to obtain a hMPV test piece (test device).

6. Preparation of Specimen Extract

This will be described in each of Examples below.

Example 1 Verification of False Negative Suppression Effect Using Nasal Aspirate Specimen in hMPV Antigen Detection Immunochromatography A mixture containing 50 mM Tris buffer (pH 8.0), and 2% (w/v) polyoxyethylene octylphenyl ether (trade name: Triton X-100 (manufactured by Nacalai Tesqhe, Inc.), hereinafter referred to as Triton X-100) was prepared to be used as a specimen extracting solution of Control 1. Next, for verifying EDTA and EGTA as a chelating agent, specimen extracting solutions having respective compositions were prepared (see Table 1 for details).

A swab (Ex Swab-002; manufactured by Denka Company Limited) was soaked with a nasal aspirate, which was suspended in 400 μL of each of the specimen extracting solutions having the respective compositions. Inactivated hMPV was added thereto in an amount of 30 μL to be mixed. 50 μL of each of the resultant mixtures was dropped onto a sample pad portion of the hMPV test piece, and visual determination was performed after 5 minutes.

TABLE 1

Specimen Extracting Solution Compositions

| No. | Composition of Specimen Extracting Solution |
|---|---|
| control | 50 mM Tris(pH 8.0), 2% TritonX-100 |
| 1 | 50 mM Tris(pH 8.0), 2% TritonX-100, 5 mM EDTA |
| 2 | 50 mM Tris(pH 8.0), 2% TritonX-100, 10 mM EDTA |
| 3 | 50 mM Tris(pH 8.0), 2% TritonX-100, 20 mM EDTA |
| 4 | 50 mM Tris(pH 8.0), 2% TritonX-100, 30 mM EDTA |
| 5 | 50 mM Tris(pH 8.0), 2% TritonX-100, 50 mM EDTA |
| 6 | 50 mM Tris(pH 8.0), 2% TritonX-100, 150 mM EDTA |
| 7 | 50 mM Tris(pH 8.0), 2% TritonX-100, 300 mM EDTA |
| 8 | 50 mM Tris(pH 8.0), 2% TritonX-100, 500 mM EDTA |
| 9 | 50 mM Tris(pH 8.0), 2% TritonX-100, 50 mM EGTA |

As a result, when testing with the nasal aspirate, false negative result was observed with the control condition without any chelating agents but when EDTA and EGTA, that is, a chelating agent, were used in a concentration of 10 mM or more, false negative could be suppressed, and this effect was particularly high when the concentration was in a range from 50 mM to 300 mM. Results thus obtained are shown in Table 2.

TABLE 2

False Negative Suppression Effect in Nasal Aspirate Specimen by Chelating Agent (hMPV)

| | Specimen Treatment Solution No. | | | | | | | | |
|---|---|---|---|---|---|---|---|---|---|
| | control | 1 | 2 | 3 | 4 | 5 | 6 | 7 | 9 |
| Chelating Agent Concentration (mM) | 0 | 5 | 10 | 20 | 30 | 50 | 150 | 300 | 50 |
| False Negative Suppression Effect | X | X | Δ | Δ | ○ | ⊙ | ⊙ | ⊙ | ⊙ |

X: no false negative suppression effect attained
Δ: false negative suppression effect rather attained
○: false negative suppression effect attained
⊙: false negative suppressed

Example 2 Verification of False Negative Suppression Effect Using hMPV-Positive Nasal Aspirate Specimen in hMPV Antigen Detection Immunochromatography The specimen extract No. 5 containing the 50 mM chelating agent, which was found to be high in the effect in Example 1, was used to verify the false negative suppressing effect using a hMPV-positive nasal aspirate specimen in the hMPV antigen detection immunochromatography.

A swab (Ex Swab-002; manufactured by Denka Company Limited) was soaked with a hMPV-positive nasal aspirate, which was suspended in 400 μL of each of the specimen extracting solutions having the respective compositions. 50 μL of each of the resultant mixtures was dropped onto the sample pad portion of the hMPV test piece, and visual determination was performed after 5 minutes.

As a result, the false negative could be suppressed also in the hMPV-positive nasal aspirate specimen by using the specimen extracting solution No. 5 in the same manner as in Example 1. Results are all shown in Table 3.

TABLE 3

| False Negative Suppression Effect in hMPV-positive Nasal Aspirate Specimen by Chelating Agent | | |
|---|---|---|
| | Specimen Treatment Solution No. | |
| | control | 5 |
| Chelating Agent Concentration (mM) | 0 | 50 |
| False Negative Suppression Effect | X | ⊙ |

X: no false negative suppression effect attained
⊙: false negative suppressed

Example 3 Verification of False Negative Suppression Effect Using Saliva Specimen in hMPV Antigen Detection Immunochromatography The specimen extracting solutions having the respective compositions shown in Table 1 were used to verify the false negative suppression effect using a saliva specimen in the hMPV antigen detection immunochromatography.

A swab (Ex Swab-001; manufactured by Denka Company Limited) was put in the mouth to be well soaked with the saliva, which was suspended in 400 μL of each of the specimen extracting solutions having the respective compositions. Inactivated hMPV was added thereto in an amount of 30 μL to be mixed. 50 μL of each of the resultant mixtures was dropped onto the sample pad portion of the hMPV test piece, and visual determination was performed after 5 minutes.

As a result, false negative result was observed with the control condition using the saliva, but when EDTA, that is, a chelating agent, was used in a concentration of 10 mM or more, false negative could be suppressed, and this effect was particularly high when the concentration was in a range from 50 mM to 300 mM. Results thus obtained are shown in Table 4.

TABLE 4

| False Negative Suppression Effect in Saliva Specimen by Chelating Agent (hMPV) | | | | | | |
|---|---|---|---|---|---|---|
| | Specimen Extracting Solution No. | | | | | |
| | control | 1 | 2 | 5 | 6 | 7 |
| Chelating Agent Concentration (mM) | 0 | 5 | 10 | 50 | 150 | 300 |
| False Negative Suppression Effect | X | X | Δ | ○ | ⊙ | ○ |

X: no false negative suppression effect attained
Δ: false negative suppression effect rather attained
○: false negative suppression effect attained
⊙: false negative suppressed

Example 4 Verification of False Positive Suppression Effect Using Saliva Specimen in hMPV Antigen Detection Immunochromatography The specimen extracting solutions having the respective compositions shown in Table 1 were used to verify the false positive suppression effect using a saliva specimen in the hMPV antigen detection immunochromatography.

A swab (Ex Swab-001; manufactured by Denka Company Limited) was put in the mouth to be well soaked with the saliva, which was suspended in 400 μL of each of the specimen extracting solutions having the respective compositions. Inactivated hMPV was added thereto in an amount of 30 μL to be mixed. 50 μL of each of the resultant mixtures was dropped onto the sample pad portion of the hMPV test piece, and visual determination was performed after 5 minutes.

As a result, false positive of the control was caused in using the saliva, but when EDTA, that is, a chelating agent, was used in a concentration of 50 mM or more, false positive could be suppressed. Results thus obtained are shown in Table 5.

TABLE 5

| False Positive Suppression Effect in Saliva Specimen by Chelating Agent (hMPV) | | | | | | |
|---|---|---|---|---|---|---|
| | Specimen Treatment Solution No. | | | | | |
| | control | 1 | 2 | 5 | 6 | 7 |
| Chelating Agent Concentration (mM) | 0 | 5 | 10 | 50 | 150 | 300 |
| False Positive Suppression Effect | X | X | X | ⊙ | ⊙ | ⊙ |

X: no false positive suppression effect attained
Δ: false positive suppression effect rather attained
○: false positive suppression effect attained
⊙: false positive suppressed

Example 5 Verification of False Negative Suppression Effect Using hMPV-positive Nasal Aspirate Specimen in Accordance with Timing of Contact Between Specimen, Antigen Contained in Specimen and Chelating Agent in hMPV Antigen Detection Immunochromatography The false negative suppression effect using a hMPV-positive nasal aspirate specimen in accordance with timing of contact between a specimen, an antigen contained in the specimen and a chelating agent in the hMPV antigen detection immunochromatography was verified under each of conditions shown in Table 6.

TABLE 6

| Conditions for Verifying False Negative Suppression Effect Using hMPV-positive Nasal Aspirate Specimen | | |
|---|---|---|
| | Composition of Specimen Extracting Solution in Suspending Specimen (final concentration) | Composition of Solution Added After Suspending Specimen (final concentration) |
| condition 1 | 50 mM Tris(pH8.0), 2% TritonX-100 | none |
| condition 2 | 50 mM Tris(pH8.0), 2% TritonX-100 | 50 mM EDTA |
| condition 3 | 50 mM Tris(pH8.0) | 2% TritonX-100, 50 mM EDTA |
| condition 4 | 50 mM Tris(pH8.0), 50 mM EDTA | 2% TritonX-100 |

A swab (Ex Swab-002; manufactured by Denka Company Limited) was soaked with a hMPV-positive nasal aspirate, which was suspended in 400 μL of each of the specimen extracting solutions having the respective compositions as described in Table 6. To each of the thus obtained suspensions, 2% (w/v) Triton X-100 and 50 mM EDTA were added under each of the conditions shown in Table 6, and thus, it was verified whether the false negative suppressing effect is affected by the presence of EDTA in virus destruction with 2% (w/v) Triton X-100. 50 μL of each of mixtures obtained under the respective conditions was dropped onto the sample pad portion of the hMPV test piece, and visual determination was performed after 5 minutes.

As a result, the false negative result was observed in using the nasal aspirate under the conditions 1 and 2, but the false negative could be suppressed under the conditions 3 and 4. Results thus obtained are shown in Table 7.

TABLE 7

| | Specimen Treatment Solution No. | | | |
|---|---|---|---|---|
| | condition 1 | condition 2 | condition 3 | condition 4 |
| False Positive Suppression Effect | X | X | ○ | ○ |

X: no false positive suppression effect attained
○: false positive suppression effect attained Based on this result, it was presumed that the false negative suppression effect can be obtained in using a hMPV-positive nasal aspirate specimen when EDTA is present in virus destruction with Triton X-100.

Example 6 Comparison in Coloring Intensity Between Specimen Extracting Solution and Control Specimen Extracting Solution in hMPV Antigen Detection Immunochromatography The specimen extracting solutions having the respective compositions shown in Table 1 were used to perform a comparison test in coloring intensity between a specimen extracting solution and a conventional specimen extracting solution in the hMPV antigen detection immunochromatography.

To 400 μL of each of the specimen extracting solutions having the respective components, 30 μL of inactivated hMPV was added to be mixed. 50 μL of each of the resultant mixtures was dropped onto the sample pad portion of the hMPV test piece, and visual determination was performed after 5 minutes.

As a result, coloring was caused in using the control specimen extracting solution and the specimen extracting solutions Nos. 1 to 7, but was not caused in using the specimen extracting solution No. 8. Besides, coloring intensity was lowered in using the specimen extracting solution No. 7, and when EDTA was used in a concentration range of 10 to 150 mM, the specificity could be improved without reducing signal intensity. Results thus obtained are shown in Table 8. It is noted that the coloring intensities of +, ++, and +++ indicate that signals are stronger in this order, and that 0 indicates the there is no color intensity observed.

TABLE 8

Comparison in Coloring Intensity Between Specimen Extracting Solution and Conventional Specimen Extracting Solution (hMPV)

| | Specimen Treatment Solution No. | | | | | | | | |
|---|---|---|---|---|---|---|---|---|---|
| | control | 1 | 2 | 3 | 4 | 5 | 6 | 7 | 8 |
| Chelating Agent Concentration (mM) | 0 | 5 | 10 | 20 | 30 | 50 | 150 | 300 | 500 |
| Signal Intensity | +++ | +++ | +++ | +++ | +++ | +++ | ++ | + | 0 |

INDUSTRIAL APPLICABILITY

A method of the present invention can be employed for accurate detection of various substances.

REFERENCE SIGNS LIST

1 nitrocellulose membrane
2 labeling material part
3 detection part
4 sample addition part
5 absorption pad part
6 plastic plate It is noted that all publications, patents and patent applications cited herein are incorporated herein by reference in their entirety.

The invention claimed is:

1. A method for detecting a target substance in a specimen, the method comprising:

contacting the specimen with a chelating agent by:

(i) putting the specimen in a specimen extracting solution containing the chelating agent and adding the specimen extracting solution to an immunochromatographic test device; or (ii) adding the specimen to an immunochromatographic test device including a portion impregnated with a specimen extracting solution containing the chelating agent; and detecting the target substance using immunochromatography, wherein an antibody is located on the immunochromatographic test device and labeled with a color latex particle, wherein:

the chelating agent is present in the specimen extracting solution at a concentration of 50 mM to 100 mM;

the target substance is selected from the group consisting of a viral antigen, a bacterial antigen, and a protein antigen;

the specimen is selected from the group consisting of a nasal swab specimen, a nasal aspirate specimen, a nasal wash specimen, a blown snot specimen, a pharyngeal swab specimen, and a saliva specimen; and the contacting suppresses signal reduction caused by a false negative reaction or a false positive reaction.

2. The method according to claim 1, wherein the method for detecting the target substance comprises (i) putting the specimen in a specimen extracting solution containing the chelating agent and adding the specimen extracting solution to an immunochromatographic test device.

3. The method according to claim 2, wherein the specimen extracting solution further contains a surfactant.

4. The method according to claim 1, wherein the method for detecting the target substance comprises (ii) adding the specimen to an immunochromatographic test device including a portion impregnated with a specimen extracting solution containing the chelating agent.

5. The method according to claim 1, wherein the chelating agent is selected from the group consisting of ethylenediaminetetraacetic acid (EDTA), glycoletherdiaminetetraacetic acid (EGTA), 1,3-propanediaminetetraacetic acid (PDTA), and nitrilotriacetic acid (NTA).

* * * * *